US006946433B2

(12) United States Patent
Green et al.

(10) Patent No.: US 6,946,433 B2
(45) Date of Patent: Sep. 20, 2005

(54) TEXTILES HAVING A WASH-DURABLE SILVER-ION BASED ANTIMICROBIAL TOPICAL TREATMENT

(75) Inventors: David E. Green, Simpsonville, SC (US); Leland G. Close, Jr., Spartanburg, SC (US); Dirk L. Van Hyning, Spartanburg, SC (US)

(73) Assignee: Milliken & Company, Spartanburg, SC (US)

(*) Notice: Subject to any disclaimer, the term of this patent is extended or adjusted under 35 U.S.C. 154(b) by 247 days.

(21) Appl. No.: 10/146,684

(22) Filed: May 15, 2002

(65) Prior Publication Data

US 2002/0192386 A1 Dec. 19, 2002

Related U.S. Application Data

(62) Division of application No. 09/586,081, filed on Jun. 2, 2000, now abandoned.

(51) Int. Cl.$^7$ .............................. C11D 9/50; B05D 1/36; B23P 17/00
(52) U.S. Cl. ...................... 510/319; 424/406; 29/527.7; 442/123; 427/412; 428/340; 428/341; 428/342; 252/8.82; 8/115.51
(58) Field of Search .......................... 510/319; 424/406, 424/404; 29/527.7; 442/123; 427/412; 428/340–342; 252/8.82; 8/115.51

(56) References Cited

U.S. PATENT DOCUMENTS

| 5,849,311 A | * 12/1998 | Sawan et al. ............... 424/406 |
| 6,454,813 B1 | * 9/2002 | Chan ......................... 8/115.51 |
| 6,461,386 B1 | * 10/2002 | Chan et al. ................. 8/115.51 |
| 6,584,668 B2 | * 7/2003 | Green et al. ............... 29/527.2 |

* cited by examiner

Primary Examiner—Margaret Einsmann
Assistant Examiner—Preeti Kumar
(74) Attorney, Agent, or Firm—Terry T. Moyer; Brenda D. Wentz

(57) ABSTRACT

Durable antimicrobial treatments for textile fabrics are provided. Such treatments preferably comprise silver ions, particularly as constituents of inorganic metal salts or zeolites. This particular treatment requires the presence of a resin binder, either as a silver-ion overcoat or as a component of a dye bath mixture admixed with the silver-ion antimicrobial compound. Such a treatment is extremely durable on such substrates; after a substantial number of standard launderings and dryings, the treatment does not wear away in any appreciable amount and thus the substrate retains its antimicrobial activity. The particular treatment method, as well as the treated textile fabrics are also encompassed within this invention.

8 Claims, No Drawings

TEXTILES HAVING A WASH-DURABLE SILVER-ION BASED ANTIMICROBIAL TOPICAL TREATMENT

CROSS REFERENCE TO RELATED APPLICATIONS

This application is a divisional of co-pending application Ser. No. 09/586,081, filed on Jun. 2, 2000 now abandoned.

FIELD OF THE INVENTION

This invention relates to improvements in durable antimicrobial treatments for textile fabrics. Such treatments preferably comprise silver ions, particularly as constituents of inorganic metal salts or zeolites. This particular treatment requires the presence of a resin binder, either as a silver-ion overcoat or as a component of a dye bath mixture admixed with the silver-ion antimicrobial compound. Such a treatment is extremely durable on such substrates; after a substantial number of standard launderings and dryings, the treatment does not wear away in any appreciable amount and thus the substrate retains its antimicrobial activity. The particular treatment method, as well as the treated textile fabrics are also encompassed within this invention.

DISCUSSION OF THE PRIOR ART

There has been a great deal of attention in recent years given to the hazards of bacterial contamination from potential everyday exposure. Noteworthy examples of such concern include the fatal consequences of food poisoning due to certain strains of *Eschericia coli* being found within undercooked beef in fast food restaurants; Salmonella contamination causing sicknesses from undercooked and unwashed poultry food products; and illnesses and skin infections attributed to *Staphylococcus aureus, Klebsiella pneumoniae*, yeast, and other unicellular organisms. With such an increased consumer interest in this area, manufacturers have begun introducing antimicrobial agents within various household products and articles. For instance, certain brands of polypropylene cutting boards, liquid soaps, etc., all contain antimicrobial compounds. The most popular antimicrobial for such articles is triclosan. Although the incorporation of such a compound within liquid or polymeric media has been relatively simple, other substrates, including the surfaces of textiles and fibers, have proven less accessible. There is a long-felt need to provide effective, durable, and long-lasting antimicrobial characteristics for textile surfaces, in particular on apparel fabrics, and on film surfaces. Such proposed applications have been extremely difficult to accomplish with triclosan, particularly when wash durability is a necessity (triclosan easily washes off any such surfaces). Furthermore, although triclosan has proven effective as an antimicrobial compound, the presence of chlorines and chlorides within such a compound causes skin irritation which makes the utilization of such with fibers, films, and textile fabrics for apparel uses highly undesirable. Furthermore, there are commercially available textile products comprising acrylic and/or acetate fibers co-extruded with triclosan (for example Celanese markets such acetate fabrics under the name Microsafe™ and Acordis markets such acrylic fibers, either under the tradename Amicor™). However, such an application is limited to those types of fibers; it does not work specifically for and within polyester, polyamide, cotton, spandex, etc., fabrics. Furthermore, this co-extrusion procedure is very expensive.

Silver-containing inorganic microbiocides have recently been developed and utilized as antimicrobial agents on and within a plethora of different substrates and surfaces. In particular, such microbiocides have been adapted for incorporation within melt spun synthetic fibers, as taught within Japanese unexamined Patent Application No. H11-124729, in order to provide certain fabrics which selectively and inherently exhibit antimicrobial characteristics. Furthermore, attempts have been made to apply such specific microbiocides on the surfaces of fabrics and yarns with little success from a durability standpoint. A topical treatment with such compounds has never been successfully applied as a durable finish or coating on a fabric or yarn substrate. Although such silver-based agents provide excellent, durable, antimicrobial properties, to date such is the sole manner available within the prior art of providing a long-lasting, wash-resistant, silver-based antimicrobial textile. However, such melt spun fibers are expensive to make due to the large amount of silver-based compound required to provide sufficient antimicrobial activity in relation to the migratory characteristics of such a compound within the fiber itself to its surface. A topical coating is also desirable for textile and film applications, particularly after finishing of the target fabric or film. Such a topical procedure permits treatment of a fabric's individual fibers prior to or after weaving, knitting, and the like, in order to provide greater versatility to the target yarn without altering its physical characteristics. Such a coating, however, must prove to be wash durable, particularly for apparel fabrics, in order to be functionally acceptable. Furthermore, in order to avoid certain problems, it is highly desirable for such a metallized treatment to be electrically non-conductive on the target fabric, yarn, and/or film surface. With the presence of metals and metal ions, such a wash durable, non-electrically conductive coating has not been available in the past. Such an improvement would thus provide an important advancement within the textile, yarn, and film art. Although antimicrobial activity is one desired characteristic of the inventive metal-treated fabric, yarn, or film, this is not a required property of the inventive article. Odor-reduction, heat retention, distinct coloriations, reduced discolorations, improved yarn and/or fabric strength, resistance to sharp edges, etc., are all either individual or aggregate properties which may be accorded the user of such an inventive treated yarn, fabric, or film.

DESCRIPTION OF THE INVENTION

It is thus an object of the invention to provide a simple manner of effectively treating a textile with a wash-durable antimicrobial silver-ion containing treatment. Another object of the invention is to provide an aesthetically pleasing metal-ion-treated textile which is wash durable, non-yellowing, non-irritating to skin, and which provides antimicrobial properties.

Accordingly, this invention encompasses a treated substrate comprising a finish comprising silver-ion containing compound and a fabric substrate; wherein said compound is present on at least a portion of the surface of said substrate; and wherein said treated substrate exhibits a log kill rate for *Staphylococcus aureus* of at least 1.5, preferably above 2.0, more preferably above 3.0, and a log kill rate for *Klebsiella pneumoniae* of at least 1.5, preferably above 2.0, and more preferably above 3.0, both as tested in accordance with AATCC Test Method 100-1993 for 24 hour exposure, after at least 10 washes, said washes being performed in accordance with the wash procedure as part of AATCC Test Method 130-1981. Even more preferable log kill rates exhibited by the inventive treated substrates are at least 3.2 and 3.2, respectively for *S. aureus* and *K. pneumoniae*; still more preferably these log kill rates are 3.5 and 3.5, respectively; and most preferably these are 4.0 and 4.0, respectively. Such an invention also encompasses the different methods of producing such a treated substrate. The wash durability test noted above is standard and, as will be well appreciated by one of ordinary skill in this art, is not intended to be a required or limitation within this invention. Such a test method merely provides a standard which, upon 10 washes in accordance with such, the inventive treated substrate will not lose an appreciable amount of its electrically non-conductive metal finish.

Nowhere within the prior art has such a specific treated substrate or method of making thereof been disclosed, utilized, or fairly suggested. The closest art is a product marketed under the tradename X-STATIC® which is a fabric article electrolessly plated with a silver coating. Such a fabric is highly electrically conductive and is utilized for static charge dissipation. Also, the coating alternatively exists as a removable silver powder finish on a variety of surfaces. The aforementioned Japanese patent publication to Kuraray is limited to fibers within which a silver-based compound has been incorporated through melt spun fiber techniques. Nowhere has such a wash-durable topical treatment as now claimed been mentioned or alluded to.

Any fabric may be utilized as the substrate within this application. Thus, natural (cotton, wool, and the like) or synthetic fibers (polyesters, polyamides, polyolefins, and the like) may constitute the target substrate, either by itself or in any combinations or mixtures of synthetics, naturals, or blends or both types. As for the synthetic types, for instance, and without intending any limitations therein, polyolefins, such as polyethylene, polypropylene, and polybutylene, halogenated polymers, such as polyvinyl chloride, polyesters, such as polyethylene terephthalate, polyester/polyethers, polyamides, such as nylon 6 and nylon 6,6, polyurethanes, as well as homopolymers, copolymers, or terpolymers in any combination of such monomers, and the like, may be utilized within this invention. Nylon 6, Nylon 6,6, polypropylene, and polyethylene terephthalate (a polyester) are particularly preferred. Additionally, the target fabric may be coated with any number of different films, including those listed in greater detail below. Furthermore, the substrate may be dyed or colored to provide other aesthetic features for the end user with any type of colorant, such as, for example, poly(oxyalkylenated) colorants, as well as pigments, dyes, tints, and the like. Other additives may also be present on and/or within the target fabric or yarn, including antistatic agents, brightening compounds, nucleating agents, antioxidants, UV stabilizers, fillers, permanent press finishes, softeners, lubricants, curing accelerators, and the like. Particularly desired as optional and supplemental finishes to the inventive fabrics are soil release agents which improve the wettability and washability of the fabric. Preferred soil release agents include those which provide hydrophilicity to the surface of polyester. With such a modified surface, again, the fabric imparts improved comfort to a wearer by wicking moisture. The preferred soil release agents contemplated within this invention may be found in U.S. Pat. Nos. 3,377,249; 3,540,835; 3,563,795; 3,574,620; 3,598,641; 3,620,826; 3,632,420; 3,649,165; 3,650,801; 3,652,212; 3,660,010; 3,676,052; 3,690,942; 3,897,206; 3,981,807; 3,625,754; 4,014,857; 4,073,993; 4,090,844; 4,131,550; 4,164,392; 4,168,954; 4,207,071; 4,290,765; 4,068,035; 4,427,557; and 4,937,277. These patents are accordingly incorporated herein by reference. Additionally, other potential additives and/or finishes may include water repellent fluorocarbons and their derivatives, silicones, waxes, and other similar waterproofing materials.

The particular treatment must comprise at least one type of silver-ion containing compounds, or mixtures thereof of different types. The term silver-ion containing compounds encompasses compounds which are either ion-exchange resins, zeolites, or, possibly substituted glass compounds (which release the particular metal ion bonded thereto upon the presence of other anionic species). The preferred metal-ion containing compound for this invention is an antimicrobial silver zirconium phosphate available from Milliken & Company, under the tradename ALPHASAN®. Other potentially preferred silver-containing antimicrobials in this invention is a silver-substituted zeolite available from Sinanen under the tradename ZEOMIC® AJ, or a silver-substituted glass available from Ishizuka Glass under the tradename IONPURE®, may be utilized either in addition to or as a substitute for the preferred species. Generally, such a metal compound is added in an amount of from about 0.01 to about 40% by total weight of the particular treatment composition; more preferably from about 0.05 to about 30%; and most preferably from about 0.1 to about 30%. Preferably this metal compound is present in an amount of from about 0.01 to about 5% owf, preferably from about 0.05 to about 3% owf, more preferably from about 0.1 to about 2% owf, and most preferably about 1.0% owf. The treatment itself, including any necessary binders, leveling agents, adherents, thickeners, and the like, is added to the substrate in an amount of about 0.01 to about 10% owf.

The binder material, which, although optional, does provide highly beneficial durability for the inventive yarns, is preferably selected from a permanent press type resin and an acrylic type resin. Such resins provide washfastness by adhering silver to the target yarn and/or fabric surface.

The selected substrate may be any fabric comprising individual fibers or yarns of any typical source for utilization within fabrics, including natural fibers (cotton, wool, ramie, hemp, linen, and the like), synthetic fibers (polyolefins, polyesters, polyamides, polyaramids, acetates, rayon, acylics, and the like), and inorganic fibers (fiberglass, boron fibers, and the like). The yarn or fiber may be of any denier, may be of multi- or mono-filament, may be false-twisted or twisted, or may incorporate multiple denier fibers or filaments into one single yarn through twisting, melting, and the like. The target fabrics may be produced of the same types of yarns discussed above, including any blends thereof. Such fabrics may be of any standard construction, including knit, woven, or non-woven forms. The inventive fabrics may be utilized in any suitable application, including, without limitation, apparel, upholstery, bedding, wiping cloths, towels, gloves, rugs, floor mats, drapery, napery, bar runners, textile bags, awnings, vehicle covers, boat covers, tents, and the like. The inventive fabric may also be coated, printed, colored, dyed, and the like.

The preferred procedures utilizing silver-ion containing compounds, such as either ALPHASAN®, ZEOMIC®, or IONPURE® as preferred compounds (although any similar types of compounds which provide silver ions may also be utilized), exhausted on the target fabric or film surface and then overcoated with a binder resin. Alternatively, the silver-ion containing compound may be admixed with a binder within a dye bath, into which the target fabric is then immersed at elevated temperatures (i.e., above about 50° C.).

Such a procedure was developed through an initial attempt at understanding the ability of such metal-ion containing compounds to attach to a fabric surface. Thus, a sample of ALPHASAN® was first exhausted from a dye bath on to a target polyester fabric surface. The treated fabric exhibited excellent log kill rate characteristics; however, upon washing in a standard laundry method (AATCC Test Method 130-1981, for instance), the antimicrobial activity was drastically reduced. Such promising initial results led to the inventive wash-durable antimicrobial treatment wherein the desired metal-ion containing compound would be admixed or overcoated with a binder resin on the target fabric surface. It was determined that proper binder resins are selected from the group consisting of nonionic permanent press binders (i.e., cross-linked adhesion promotion compounds, including, without limitation, cross-linked imidazolidinones, available from Sequa under the tradename Permafresh®) or slightly anionic binders (including, without limitation, acrylics, such as Rhoplex® TR3082 from Rohm & Haas). Other nonionics and slightly anionics may be utilized as long as they provide the desired adhesion characteristics. Such potential compounds include melamine formaldehyde, melamine urea, ethoxylated polyesters (such as Lubril QCX™, available from Rhodia, and the like. The initial exhaustion of ALPHASAN® is thus preferably followed by a thin coating of binder resin to provide the desired wash durability characteristics for the metal-based particle treatment. Such a binder resin is necessarily neither cationic nor strongly anionic in nature due to problems involved with any such ionic species and the ability to provide long-term durability on the fabric surface. With such specific binder materials utilized, the antimicrobial characteristics of the treated fabric remained very effective for the fabric even after as many as ten standard laundering procedures.

Also possible, though less effective as compared to the aforementioned binder resin overcoat, but still an acceptable method of providing a wash-durable antimicrobial metal-treated fabric surface, is the application of a silver-ion containing compound/binder resin from a dye bath mixture. The exhaustion of such a combination is less efficacious from an antimicrobial activity standpoint than the other overcoat, but, again, still provides a wash-durable treatment with acceptable antimicrobial benefits. In actuality, this mixture of compound/resin may be applied through spraying, dipping, padding, and the like.

The preferred embodiments of these alternatives fabric treatments are discussed in greater detail below.

DESCRIPTION OF THE PREFERRED EMBODIMENTS

Initially, dispersions of ALPHASAN® (silver-based ion exchange compound available from Milliken & Company) were applied in a dye bath exhaustion without any binder resin present. After exhaustion was completed, atomic absorption data was collected and analyzed which showed an actual average active level of 0.9% owf (showing a retention of about 90% of the active ingredient on the fabric). The results on four samples of a 100% polyester fabric, applied at a temperature of about 280° F. (for 2 samples) and 265° F. (for the remaining 2 samples) with an exhaustion level of the silver-based compound of about 1.0% owf, and heat-set at a temperature of about 380° F., for the log kill rate of S. aureus and K. pneumoniae, are as follows:

TABLE 1

Log Kill Rates After Multiple Washings With No Binder Resin

| Dye Temp. | # of Washes | Log Kill Rate for S. aureus | Log Kill Rate for K. pneumoniae |
|---|---|---|---|
| 280° F. | 0 | 4.59 | 4.50 |
| 280° F. | 1 | 2.00 | 2.70 |
| 265° | 0 | 4.40 | 3.80 |
| 265° | 1 | 2.10 | 3.00 |

Even after 1 wash, reductions in antimicrobial activity were pronounced. Thus further improvements with binder resin technologies were developed to increase the wash durability.

Examples of particularly preferred fabrics and fabric treatments within the scope of the present invention are set forth below.

1) Exhaustion of Compound Followed with Binder Resin Overcoat a) Acrylic Binder Resin—A dispersion of ALPHASAN® (silver-based ion exchange compound available from Milliken & Company) was first produced through the mixing of about 30% by weight of the silver-based compound, about 23.0% by weight of a mixture of anionic surfactants, Tamol® SN, available from Rohm & Haas, and Synfac® 8337, available from Milliken & Company, and the remainder water. This dispersion was then applied through exhaustion within a dye bath to four fabric samples (all of 100% polyester construction; with 51 picks by 52 ends; 300 denier multifilament yarn). Two were dyed at a temperature of about 280° F.; the others at a temperature of about 265° F. The exhaustion level of the active ALPHASAN® compounds on the target fabrics was about 1.0% owf. The fabrics were then coated with an acrylic binder material, Rhoplex® TR3082, in an amount of about 2.5% owf. The coated fabrics were then heat-set at 380° F. The log kill rate for unwashed fabrics for S. aureus was measured to be 4.9; for K. pneumoniae, 2.54. The results after multiple washings are tabulated below:

TABLE 2

Log Kill Rates After Multiple Washings With Acrylic Overcoat

| Number of Washes | Log Kill Rate for S. aureus | Log Kill Rate for K. pneumoniae |
|---|---|---|
| 1 | 4.59 | 2.28 |
| 5 | 4.15 | 2.20 |
| 10 | 3.13 | 1.97 |

It is important to note, and as is well appreciated and understood by one of ordinary in the art, that variations in log kill rate measurements are prevalent, though, reliable, due to inherent difficulties in both biological testing and in the ability to establish completely controlled bacterium counts on such surfaces. These results thus show very favorable antimicrobial performance and thus excellent wash durability on the fabric surface.

b) Permanent Press Binder Resin—The same type of ALPHASAN® dispersion and exhaustion procedure was followed as above. The overcoat, however, was Permafresh®, available from Sequa. Again, about 2.5% owf of this overcoat resin was applied over the ALPHASAN®-treated fabrics. Also added within the dye bath was a butyl benzoate carrier in an amount of about 2.5% owf. The log kill results for this sample were as follows:

TABLE 3

Log Kill Rates After Multiple Washings With Permanent Press Overcoat

| Number of Washes | Log Kill Rate for S. aureus | Log Kill Rate for K. pneumoniae |
| --- | --- | --- |
| 0 | 3.21 | 5.32 |
| 1 | 4.11 | 3.89 |
| 5 | 2.98 | 3.03 |
| 10 | 3.94 | 4.23 |

Excellent durability results were thus obtained with such a system.

c) Lubril QCX™ Binder Resin—The same type of ALPHASAN® dispersion and exhaustion procedure was followed as above. The overcoat, however, was PD-92 available from Milliken & Company. Again, about 2.5% owf of this overcoat resin was applied over the ALPHASAN®-treated fabrics. Also added within the dye bath was a butyl benzoate carrier in an amount of about 2.5% owf. The log kill results for this sample were as follows:

TABLE 4

Log Kill Rates After Multiple Washings With PD-92 Overcoat

| Number of Washes | Log Kill Rate for S. aureus | Log Kill Rate for K. pneumoniae |
| --- | --- | --- |
| 0 | 3.30 | 3.36 |
| 1 | 3.15 | 2.72 |
| 5 | 3.18 | 2.26 |
| 10 | 3.03 | 1.78 |

Excellent durability results were thus obtained with such a system as well.

d) Effect of Increased amount of ALPHASAN® on Wash Durability—The same fabric treatments (with Permafresh® binder resin) as above were performed with the amount of ALPHASAN® increased to a 4% owf active addition to the target fabric surface (about 13.3% owf of the dispersion). The same padding on of the permanent press binder was followed as above. The log kill results for K. pneumoniae are as follows:

TABLE 5

Log Kill Rates With High Add-On of Silver-Based Compound

| Number of Washes | Log Kill Rate for K. pneumoniae |
| --- | --- |
| 0 | 5.6 |
| 5 | 5.7 |
| 10 | 4.4 |

Again, excellent durability was obtained.

e) Effect of Increased amount of Permanent Press Binder Resin on Wash Durability—The same fabric treatments (with Permafresh® binder resin) as above were performed with the padded on amount of binder resin increased to a 7.5% owf addition to the target fabric surface. The log kill results for K. pneumoniae are as follows:

TABLE 6

Log Kill Rates With High Add-On of Permanent Press Binder Resin

| Number of Washes | Log Kill Rate for K. pneumoniae |
| --- | --- |
| 0 | 5.7 |
| 5 | 4.0 |
| 10 | 3.9 |

Again, excellent wash durability results were obtained.

2) Exhaustion of Compound with a Binder Resin

A dispersion of ALPHASAN® (silver-based ion exchange compound available from Milliken & Company) was first produced through the mixing of about 30% by weight of the silver-based compound, about 23.0% by weight of an anionic surfactant mixture of Tamol® and Synfac® 8337 surfactant, and the remainder water. This dispersion was then applied through exhaustion within a dye bath which included an acrylic binder (Rhoplex® TR3082) which was present within the dye bath in a concentration of about 2.5% owf. A 100% polyester fabric (same as above) was then placed within the dye bath which was then heated to a temperature of about 280° F. The exhaustion level of the active ALPHASAN® compounds on the target fabrics was about 1.0% owf. The fabrics were then heat-set at 380° F. The log kill rate for unwashed fabric for S. aureus was measured to be 2.35; for K. pneumoniae, 5.38. The results after multiple washings are tabulated below:

TABLE 7

Log Kill Rates After Multiple Washings With Acrylic Resin

| Number of Washes | Log Kill Rate for S. aureus | Log Kill Rate for K. pneumoniae |
| --- | --- | --- |
| 1 | 1.50 | 2.37 |
| 5 | 1.17 | 2.37 |
| 10 | 1.36 | 2.98 |

These results show very favorable antimicrobial performance and thus excellent wash durability on the fabric surface, though less favorable than for the resin overcoated fabrics.

2) Exhaustion of Other Silver-Based Compounds

The same general exhaustion methods were followed as above with the same padding on (denoted as P in the table below) and dye bath application (D in the following table) of a permanent press binder as above as well. The different silver-based compounds applied were AmpZ200 (a TiO2/silver metal product available from DuPont), and ZEOMIC® AJ80H. The add-on weights of these were the same 1.0% owf treatment as for the ALPHASAN® noted above. The durability results for these compounds were as follows for K. pneumoniae log kill rates:

TABLE 8

Log Kill Rates With Other Silver-Based Compounds

| Compound | Number of Washes | Log Kill Rate for K. pneumoniae |
| --- | --- | --- |
| AmpZ200 (P) | 0 | 2.76 |
| AmpZ200 (P) | 10 | 1.82 |
| AmpZ200 (D) | 0 | 2.06 |
| AmpZ200 (D) | 10 | 1.36 |
| ZEOMIC ® AJ80H (P) | 0 | 5.31 |
| ZEOMIC ® AJ80H (P) | 10 | 1.64 |

TABLE 8-continued

Log Kill Rates With Other Silver-Based Compounds

| Compound | Number of Washes | Log Kill Rate for K. pneumoniae |
|---|---|---|
| ZEOMIC ® AJ80H (D) | 0 | 4.31 |
| ZEOMIC ® AJ80H (D) | 10 | 1.92 |

These are excellent durability results, although not as good as for the ALPHASAN® treatments, above.

There are, of course, many alternative embodiments and modifications of the present invention which are intended to be included within the spirit and scope of the following claims.

What is claim is:

1. A process for producing a wash durable antimicrobial treated substrate comprising an antimicrobial silver finish comprising compounds selected from the group consisting of silver-containing ion exchange compounds, silver-containing zeolites, silver-containing glass, and any mixtures thereof; and a substrate selected from the group consisting of a yarn, a fabric comprised of individual fibers, and a film;

wherein said finish is present on at least one portion of the surface of said substrate;

wherein said at least one portion of said treated substrate exhibits *Klebsiella pneumoniae* and *Staphylococcus aureus* log kill rates of at least 1.5 each in accordance with AATCC Test Method 100-1993 at an exposure of 24 hours after said substrate is washed at least 10 times in accordance with the wash procedure of AATCC Test Method 130-1981;

said process comprising the steps of a) providing said substrate;

b) providing said finish composition;

c) applying said finish composition to at least one portion of said substrate; and d) covering said finished substrate portion with a binder formulation.

2. The process of claim 1 wherein said substrate is selected from the group consisting of a textile fabric and a yarn.

3. The process of claim 1 wherein said finish comprises silver-containing ion-exchange compounds.

4. The process of claim 2 wherein said finish comprises silver-containing ion-exchange compounds.

5. A process for producing a wash durable antimicrobial treated substrate comprising an antimicrobial silver finish comprising compounds selected from the group consisting of silver-containing ion exchange compounds, silver-containing zeolites, silver-containing glass, and any mixtures thereof; and a substrate selected from the group consisting of a yarn, a fabric comprised of individual fibers, and a film;

wherein said finish is present on at least one portion of the surface of said substrate; and wherein said at least one portion of said treated substrate exhibits *Klebsiella pneumoniae* and *Staphylococcus aureus* log kill rates of at least 1.5 each in accordance with AATCC Test Method 100-1993 at an exposure of 24 hours after said substrate is washed at least 10 times in accordance with the wash procedure of AATCC Test Method 130-1981;

said process comprising the steps of a) providing said substrate;

b) providing said finish composition, wherein said composition also comprises a binding agent; and c) applying said composition of step "b" to at least one portion of said substrate.

6. The process of claim 5 wherein said substrate is selected from the group consisting of a fiber and a textile fabric.

7. The process of claim 5 wherein said finish comprises silver-containing ion-exchange compounds.

8. The process of claim 6 wherein said finish comprises silver-containing ion-exchange compounds.

* * * * *